(12) United States Patent
Stevens, Jr. et al.

(10) Patent No.: US 7,476,656 B2
(45) Date of Patent: Jan. 13, 2009

(54) FLUORESCENT AFFINITY TAG TO ENHANCE PHOSPHOPROTEIN DETECTION AND CHARACTERIZATION

(75) Inventors: Stanley Merewyn Stevens, Jr., Micanopy, FL (US); Alfred Y K Chung, Ocala, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 431 days.

(21) Appl. No.: 10/984,617

(22) Filed: Nov. 9, 2004

(65) Prior Publication Data

US 2006/0099604 A1    May 11, 2006

(51) Int. Cl.
*A61K 38/00* (2006.01)
*C12Q 1/70* (2006.01)
*C12Q 1/68* (2006.01)
*C07H 21/00* (2006.01)

(52) U.S. Cl. .................. 514/14; 435/5; 435/6; 435/7.1; 435/7.2; 536/23.1; 536/16.6

(58) Field of Classification Search .................. 514/14; 536/23.1, 26.6; 435/5, 6, 7.1, 7.2
See application file for complete search history.

(56) References Cited

OTHER PUBLICATIONS

Daugherty et al. "Quantitative Assessment of Lipoprotein Metabolism by Positron Emission Tomography with an F-containing Residualizing Label" Nucl. Med. Biol. International J. Radiat. Appl. Instrum. Part B, vol. 19, No. 3, pp. 411-416, 1992.*
Hai-Ying Gu et al. Journal of Electroanalytical Chemistry, vol. 516, 2001, pp. 119-126.*
Millot et al. Proceedings of SPIE—The International Society for Optical Engineering (1995), 2331, 34-9. (abstract only).*
Adamczyk, M. et al. "Selective analysis of phosphopeptides within a protein mixture by chemical modification, reversible biotinylation and mass spectrometry" *Rapid. Comm. Mass. Spec.* 15:1481-1488, 2001.
Fadden, P. and T.A.J. Haystead "Quantitative and selective fluorophore labeling of phosphoserine on peptides and proteins: Characterization at the attomole level by capillary electrophoresis and laser-induced fluorescence" *Anal. Biochem.* 225(1):81-88, 1995.
Goshe, M.B. et al. "Phosphoprotein isotope-coded affinity tag approach for isolating and quantitating phosphopeptides in prteome-wide analyses" Anal. Chem. 73:2578-2586, 2001.
Goshe, M.B. et al. "Phosphoprotein isotope-coded affinity tags : Application to the enrichment and identification of low-abundance phosphoproteins" *Anal. Chem.* 74:607-616, 2001.
Hastings, T.G. and E.M. Reimann "Beta-elimination of phosphate and subsequent addition of pyridoxamine as a method for identifying and sequencing peptides containing phosphoseryl residues" FEB 23(2):431-436, 1988.
Knight, Z. et al. "Phosphospecific proteolysis for mapping sites of protein phosphorylation" *Nature Biotechnol.* 21(9):1047-1054, 2003.
McLachlin, D. and B.T. Clark "Improved beta-elimination-based affinity purification strategy for enrichment of phosphopeptides" *Anal. Chem.* 75:6826-6836, 2003.
Oda, Y. et al. "Enrichment analysis of phosphorylated proteins as a tool for probing the phosphoproteome" *Nature Biotechnol.* 19:379-382, 2001.

* cited by examiner

*Primary Examiner*—Jezia Riley
(74) *Attorney, Agent, or Firm*—Saliwanchik, Lloyd & Saliwanchik

(57) ABSTRACT

The invention relates to target-associative tags incorporating cysteamine as the target-associative moiety. The invention further relates to a method for producing a target-associative tag by addition of cysteamine as the target-associative moiety to another molecule or entity having a property or properties useful in discriminating or selecting between members of a set, where such properties could include, for example, fluorescence, mass, affinity, reactivity, size, absorbance, magnetism, subatomic spin characteristics, or an ability to associate specifically or preferentially with certain structures. The invention further relates to a method for analyzing, identifying, or purifying phosphorylated proteins or phosphorylated protein fragments using a tag having the properties of both fluorescence and affinity.

26 Claims, 5 Drawing Sheets

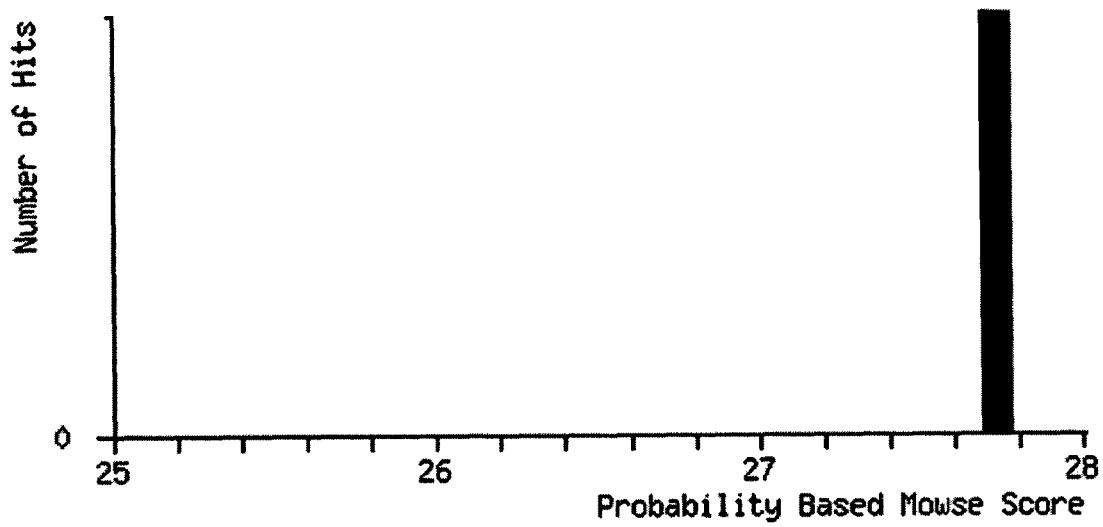

1. gi|115660      Mass: 25091    Total score: 28   Peptides matched: 1
   Beta casein precursor ☑ Check to include this hit in error tolerant search or archive report
   Query   Observed   Mr(expt)   Mr(calc)   Delta   Miss   Score   Rank   Peptide ☑   2      870.70     2609.08    2609.11    -
    0.04   0          30         1          FQSEEQQQTEDELQDK + FAT-tag (ST)

Proteins matching the same set of peptides:
gi|162797       Mass: 25072    Total score: 28   Peptides matched: 1
   beta-casein precursor
gi|162805       Mass: 25131    Total score: 28   Peptides matched: 1
   beta-casein
gi|223906       Mass: 23559    Total score: 28   Peptides matched: 1
   casein beta
gi|225825       Mass: 23608    Total score: 28   Peptides matched: 1
   beta casein
gi|416752       Mass: 24849    Total score: 28   Peptides matched: 1
   Beta casein precursor
gi|861069       Mass: 24899    Total score: 28   Peptides matched: 1
   beta-casein [Ovis aries]
gi|1168776      Mass: 24859    Total score: 28   Peptides matched: 1
   Beta casein precursor
gi|4495057      Mass: 24849    Total score: 28   Peptides matched: 1
   beta-casein [Capra hircus]
gi|4499833      Mass: 20293    Total score: 28   Peptides matched: 1
   beta-casein [Capra hircus]
gi|7441526      Mass: 23515    Total score: 28   Peptides matched: 1
   beta-casein variant CnH - bovine
gi|15425980     Mass: 24976    Total score: 28   Peptides matched: 1
   beta-casein precursor [Capra hircus]
gi|30794310     Mass: 25082    Total score: 28   Peptides matched: 1
   casein beta [Bos taurus]

FIGURE 8

FLUORESCENT AFFINITY TAG TO ENHANCE PHOSPHOPROTEIN DETECTION AND CHARACTERIZATION

FIELD OF THE INVENTION

The invention relates to target-associative tags incorporating cysteamine as the target-associative moiety. The invention further relates to a method for producing a target-associative tag by addition of cysteamine as the target-associative moiety to another molecule or entity having a property or properties useful in discriminating or selecting between members of a set, where such properties could include, for example, fluorescence, mass, affinity, reactivity, size, absorbance, magnetism, subatomic spin characteristics, or an ability to associate specifically or preferentially with certain structures. The invention further relates to a method for analyzing, identifying, or purifying phosphorylated proteins or phosphorylated protein fragments using a tag having the properties of both fluorescence and affinity.

BACKGROUND OF THE INVENTION

The subject invention relates to the art of preparing target-associative tags. Such tags are widely used in science, medicine, and elsewhere for a variety of purposes including as aids to visualization or purification. Typically, such tags comprise both a moiety having an ability to associate specifically or preferentially with certain structures ["targeting moiety"] and a moiety having a property or properties useful in discriminating or selecting between members of a set ["discriminating moiety"].

When a target-associative tag associates with its target, a tag-target conjugate is formed. In forming such a tag-target conjugate, the target typically acquires the useful property or properties of the tag. For example, an antibody-associative fluorescent tag can be associated with an antibody to confer the property of fluorescence upon the antibody. The association of the tag and the target in the tag-target conjugate can be based on the formation of one or more covalent bonds, an affinity interaction, a hydrophobic interaction, a hydrogen-bonding interaction, a magnetic interaction, or any other type of interaction that imparts an ability to associate specifically or preferentially with certain structures.

A tag-target conjugate may itself function as a target-associative tag in some cases. For example, when an antibody is tagged with a fluorophore to produce a fluorescent antibody, the fluorescent antibody can then be regarded as target-associative tag that may be directed against structures to which the antibody has an affinity.

There are a wide variety of properties that may be useful in a target-associative tag. In general, any property or properties useful in discriminating or selecting between members of a set could have utility in a target-associative tag. Such properties include, but are not limited to, fluorescence, mass, affinity, reactivity, size, absorbance, magnetism, subatomic spin characteristics, or an ability to associate specifically or preferentially with certain structures.

Practitioners skilled in the art will recognize that although target-associative tags have been described here as often comprising both a targeting moiety and a discriminating moiety, in some cases the classification of a given moiety as a targeting moiety or a discriminating moiety may be ambiguous or subject to context. For instance, a rhodamine moiety incorporated into a target-associative tag might often be regarded as a discriminating moiety in that it may exhibit fluorescence under certain conditions, but the same rhodamine moiety might also be regarded as a targeting moiety in that it may exhibit an affinity interaction with certain structures. In general, the set of all possible targeting moieties is a subset of the set of all possible discriminating moieties; every targeting moiety by definition has a property or properties useful in discriminating or selecting between members of a set in that every targeting moiety is able to specifically or preferentially associate with certain structures. In other words, every targeting moiety is also a discriminating moiety, but there may be discriminating moieties that are not targeting moieties.

While target-associative tags typically comprise both a targeting moiety and a discriminating moiety, it is possible that a single moiety could fulfill both roles. For example, in certain fluorogenic reagents known in the art it might be difficult, impossible, or simply of little descriptive utility to identify separate targeting and discriminating moieties. For example, 7-N,N-dimethylsulfonyl-4-(2,1,3-benzoxadiazolyl)isothiocyanate, also known as DBD-NCS, is a fluorogenic reagent used in peptide sequencing analysis. In associating with its target via the formation of a covalent bond, DBD-NCS is converted from a fluorogenic form to a fluorescent form. Thus the target-reactive moiety is a component of the fluorogenic/fluorescent moiety. Also, just as it is possible that a single moiety could fulfill the roles of both discriminating moiety and targeting moiety, it is also possible that a target-associative tag could contain multiple discriminating moieties or multiple targeting moieties or both.

One way of discriminating between members of a set is by fluorescent emission. For instance, the set of all structures within a cell can be differentiated by degree of fluorescence when visualizing the cell. Fluorescent target-associative tags are widely used for this purpose. For example, phalloidin is a cyclic peptide produced by the poisonous mushroom, *Amanita phalloides*. Conjugation of phalloidin as the targeting moiety and the fluorophore rhodamine as the discriminating moiety produces a target-associative tag that associates preferentially with actin bundles, allowing visualization of said actin bundles by fluorescence microscopy. Another common type of fluorescent target-associative tag is formed by conjugation of a fluorophore and an antibody. Such a fluorescent target-associative tag can be directed against structures to which the antibody has an affinity. For example, a target-associative tag consisting of the fluorophore Texas Red conjugated with a goat anti-mouse immunoglobulin can be directed against mouse primary antibodies for the purpose of visualizing cell structures.

Historically, initial difficulties in establishing the localization of phosphorylated residues in proteins led to the development of a scheme by which phosphoserine and phosphothreonine residues were modified by beta-elimination followed by nucleophilic attack to give a derivatized residue. Such a scheme has been known in the art for at least 32 years. [Simpson, D. L. et al., *Biochemistry* 111:1849-1856, 1972; Kolesnikova, V. Y. et al., *Biokhimiya* 39:235-240 (Engl. Trans.) 1974]. Subsequent refinement of the technique has frequently favored thiols as the preferred nucleophile, and the use of thiols as nucleophiles in the scheme has been known in the art for at least 25 years. [Clark, R. C. and Dijkstra, J., *Int. J. Biochem.* 11:577-585, 1979].

Many modifications of the beta-elimination/nucleophilic attack technique are known in the art, and such modifications frequently involve the use of target-associative tags as nucleophiles to imbue the derivatized phosphoresidues with a desired property. One type of modification incorporates fluorophores. Use of pyridoxamine and fluorescence detection allows detection of low picomolar quantities of a phosphorylated polypeptide. [Hastings, T. G. and Reimann E. M, *FEB* 231(2):431-436, 1988]. Use of fluorescein and laser-induced fluorescence allows detection of attomolar quantities of phosphoserine-containing peptides and proteins. [Fadden, P. and Haystead, T. A., *Anal. Biochem.* 225(1):81-88, 1995].

Another type of modification incorporates an affinity tag. Beta-elimination and subsequent nucleophilic attack by ethanedithiol, followed by addition of biotin to the resulting free thiol group, allows for affinity isolation and enrichment of protein fragments containing phosphorylated residues. [Adamczyk, M. et al., *Rapid Comm. Mass. Spec.* 15:1481-1488, 2001; Oda, Y. et al., *Nature Biotechnol.* 19:379-382, 2001]. A further refinement that utilizes nucleophilic attack by a tag containing both biotin and isotopic mass markers may be particularly useful for mass spectroscopy following affinity purification. [Goshe, M. B. et al., *Anal. Chem.* 73:2578-2586, 2001; Goshe, M. B. et al., *Anal. Chem.* 74:607-616, 2001]. An introduced thiol tag can also be used directly for affinity purification on an activated thiol resin. [McLachlin, D. T. and Chait, B. T., *Anal. Chem.* 75(24):6826-6836, 2003].

Target-associative tags that mimic lysine have been used in the beta-elimination/Michael addition scheme to introduce additional enzyme-mediated proteolysis sites at phosphoserine and phosphothreonine residues, thus facilitating the analysis of proteins containing such residues. [Knight, Z. A. et al., *Nature Biotechnol.* 21(9):1047-1054, 2003].

BRIEF SUMMARY OF THE INVENTION

The present invention pertains to methods and compositions suitable for facilitating the analysis, identification, or purification of thiol-reactive molecules. In one embodiment, the invention relates to analysis, identification, or purification of phosphoproteins. Phosphoproteins or fragments thereof may often be present in small amounts as part of complex mixtures. Incorporation of a fluorescent affinity tag (FAT) at phosphorylated residues permits both enhanced detection and facile purification with minimal sample manipulation.

In another embodiment, the invention relates the preparation of target-associative tags containing a thiol moiety. Many fluorophores, chromophores, reactive groups, magnetic particles, gold particles, isotopic mass labels, or other discriminating moieties can be usefully employed in a variety of scenarios dependent on covalent attachment of said discriminating moieties to a reactive thiol (such as a cysteamine) capable of acting as a targeting moiety. The reaction of cysteamine or cysteamine-derivatives with said discriminating moieties provides a useful way of preparing such target-associative tags.

BRIEF DESCRIPTION OF THE FIGURES

FIG. 8 presents a search of the MS/MS spectrum of the FAT-labeled HPLC-purified tryptic peptide against the nr database (NCBI) using MASCOT. A custom differential modification of serine or threonine corresponding to FAT-label addition was employed in the search.

DETAILED DESCRIPTION OF THE INVENTION

Figure 1:
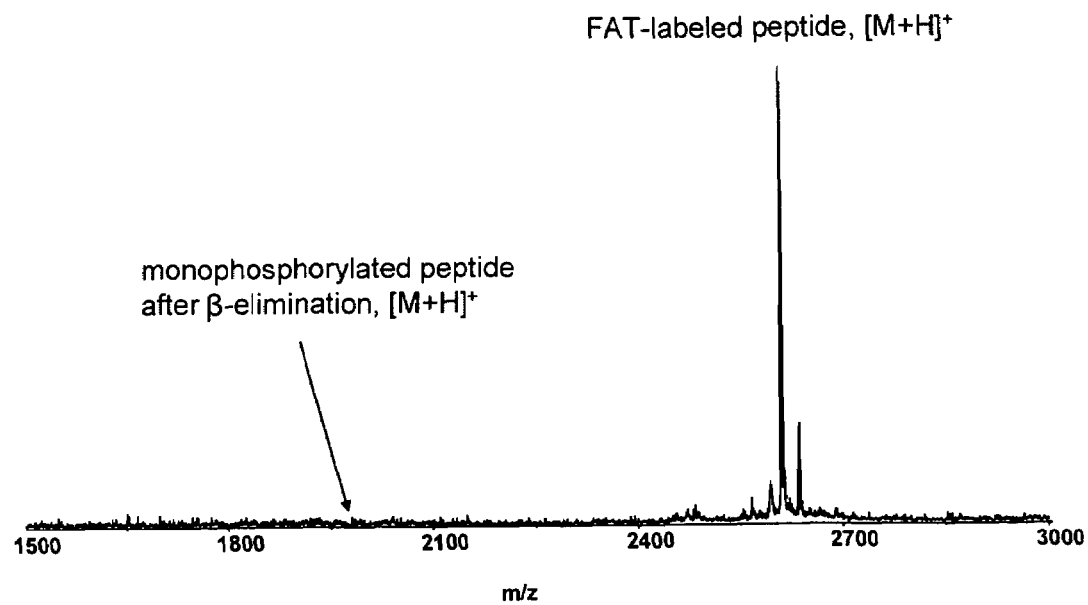
FIG. 1 depicts a MALDI-TOF mass spectrum showing reaction efficiency after beta elimination of a HPLC-purified monophoshorylated tryptic peptide of beta-casein and Michael addition of the FAT-label.

The present invention pertains to methods and compositions suitable for facilitating the analysis, identification, or purification of thiol-reactive molecules. In one embodiment, the invention relates to analysis, identification, or purification of phosphoproteins. Phosphoproteins or fragments thereof may often be present in small amounts as part of complex mixtures. Incorporation of a fluorescent affinity tag at phosphorylated residues permits both enhanced detection and facile purification with minimal sample manipulation.

Another embodiment of the subject invention provides for the labeling, identification, or purification of nucleic acids or polynucleotides containing phosphate groups (e.g., nucleotide mono-, di-, or triphosphates or polynucleotides containing phosphate groups). In various embodiments, the tags provided herein can be used in methods of detecting nucleic acid interactions (e.g., hybridization). Thus, the subject invention also provides labeled nucleic acid or polynucleotide sequences that are useful in methods such as enzymatic gene amplification (or PCR), Southern blots, Northern blots, or other techniques utilizing hybridization for the identification of polynucleotide sequences in a sample.

In another embodiment, the invention relates the preparation of target-associative tags containing a thiol moiety. Many fluorophores, chromophores, reactive groups, magnetic particles, gold particles, isotopic mass labels, or other discriminating moieties can be usefully employed in a variety of scenarios dependent on covalent attachment of said discriminating moieties to a reactive thiol capable of acting as a targeting moiety. The reaction of cysteamine or cysteamine-derivatives with said discriminating moieties provides a useful way of preparing such target-associative tags.

In preferred embodiments, the tags of the instant invention have a cysteamine moiety directly attached to discriminating moieties such as fluorophores, chromophores, reactive groups, magnetic particles, gold particles, isotopic mass labels, or other discriminating moieties; in such embodiments, linkers, such as maleimides are not used to couple the cysteamine moieties to fluorophores, chromophores, reactive groups, magnetic particles, gold particles, isotopic mass labels, or other discriminating moieties. In other embodiments of the subject invention, the fluorophores, chromophores, reactive groups, magnetic particles, gold particles, isotopic mass labels, or other discriminating moieties are not thiol reactive (i.e., these moieties attached to a cysteamine or cysteamine-containing element are not attached via the sulfur atom of the cysteamine). Non-limiting examples of fluorescent moieties that can be attached to a cysteamine moiety include rhodamine, fluorescein, coumarin, eosin, erythrosin, lucifier yellow, malachite green, or oregon green.

The subject invention further provides an exemplary fluorescent affinity tag (FAT), or composition thereof, of the formula:

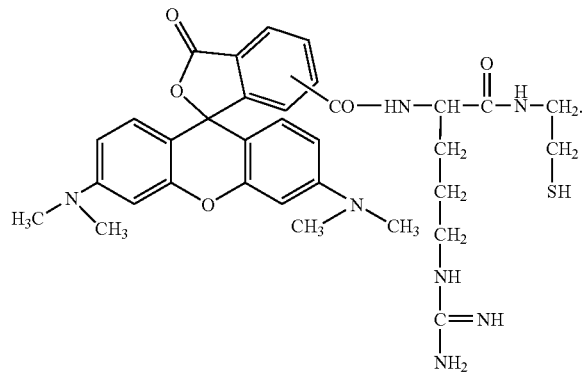

This exemplary FAT, or composition thereof, comprises rhodamine conjugated to a cysteamine moiety.

Compositions comprising the FAT of the subject invention comprise a carrier and at least one FAT. Such compositions may be formulated in any carriers, including for example, carriers described in E. W. Martin's *Remington's Pharmaceutical Science,* Mack Publishing Company, Easton, Pa. Non-limiting examples of suitable carriers include saline, phosphate buffered saline (PBS), HEPES, TRIS-based buffers, HANKS, or Ringer's solutions.

EXAMPLE 1

Purification of Affinity Tag

A microaffinity column was prepared as follows. Two microliters of Poros Protein G (Applied Biosystems) slurry was incubated with 10 µL of 1 µg/µL anti-rhodamine antibody (Abcam) solution in PBS for 1 hr at 4° C. A gel-loader tip was crimped, packed with the Protein G slurry, and washed three times with PBS.

Figure 6:
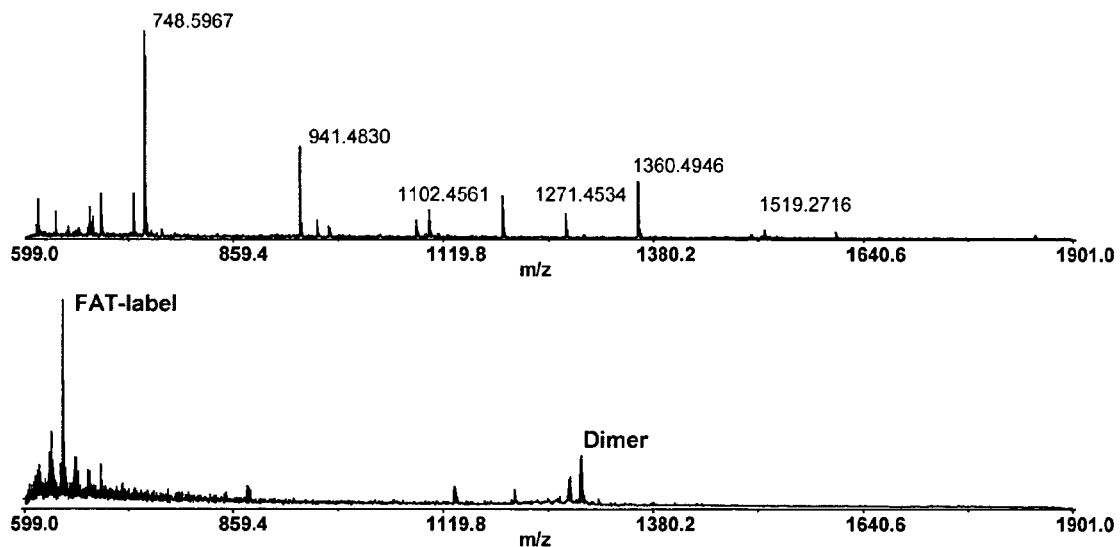
FIG. 6 depicts MALDI-TOF mass spectrum of 500 fmol myoglobin digest spiked with dilute amount of FAT reagent (top trace). The bottom trace is the same digest after affinity purification with an anti-rhodamine affinity microcolumn.

A 500 fmol myoglobin digest was prepared and spiked with a dilute amount of the FAT reagent. It was not expected that the FAT reagent would react with the peptides of the myoglobin digest because conditions for beta-elimination and Michael addition were not employed. A mass spectrum was taken of the mixture and is presented in FIG. 6 (top trace). The expected profile for the FAT reagent is not prevalent in this mass spectrum due to the relatively more abundant myoglobin-derived species.

The FAT-reagent-containing myoglobin digest was then passed through the microaffinity column several times to ensure maximum binding of the FAT reagent. The column was washed several times with 10 µL PBS to remove nonspecifically bound myoglobin-derived species. After 3×10 µL washes of water to remove excess salt, the affinity-purified FAT reagent was eluted from the column with 2 µL of 2% TFA directly onto a MALDI plate. A mass spectrum was taken of the affinity-purified elution fraction and is presented in FIG. 6 (bottom trace). Peaks attributable to the FAT reagent are now seen to be prevalent, thus indicating a substantial degree of purification of the FAT reagent.

EXAMPLE 2

Analysis by Mass Spectroscopy of FAT-Labeled HPLC-Purified Tryptic Phosphopeptide of beta-Casein A sample of beta-casein protein was digested with trypsin and the monophosphorylated peptide FQSEEQQQT-EDELQDK (SEQ ID NO: 1) was purified by HPLC. The purified tryptic peptide was subjected to conditions appropriate for beta-elimination of phosphate as described in Knight, et al.; Nat. Biotech., 2003, 21, 1047-1054. After incubation for 1-2 hours at room temperature, Michael addition of the FAT reagent was carried out for an additional 3-6 hours at room temperature.

FIG. 1 presents a mass spectrum used for general screening of reaction progress for the beta-elimination/Michael addition reactions. Ions associated with the partially derivatized peptide (i.e. after beta elimination) are present at a relatively low abundance, while ions associated with the fully derivatized peptide (i.e. after Michael addition of the FAT label) are much more prevalent.

Figure 2:
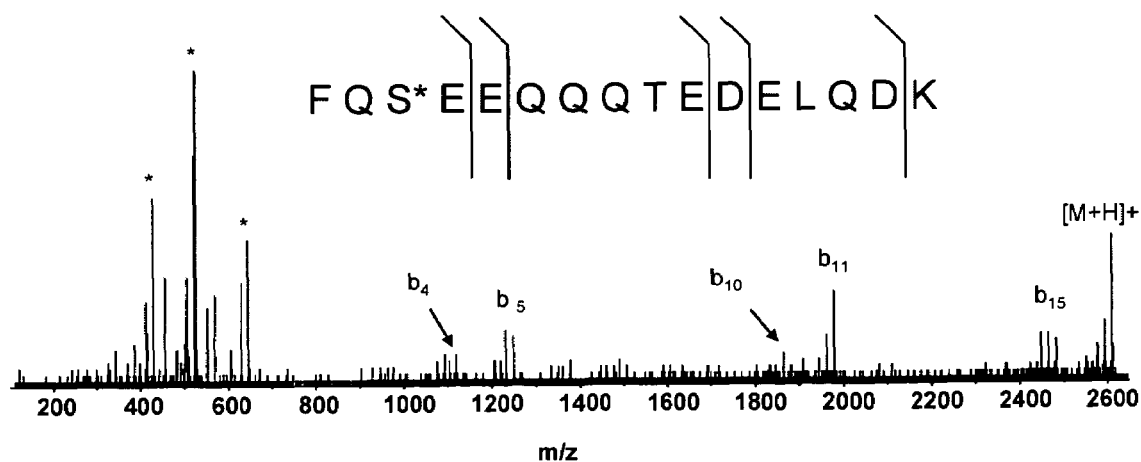
FIG. 2 illustrates a tandem mass spectrum of the FAT-labeled beta-casein tryptic peptide (SEQ ID NO: 1) acquired by a hybrid-TOF instrument (QSTAR) equipped with an oMALDI source. Asterisk (*) denotes FAT fragment ions which could be used as diagnostic ions for precursor ion scanning.
Figure 3:
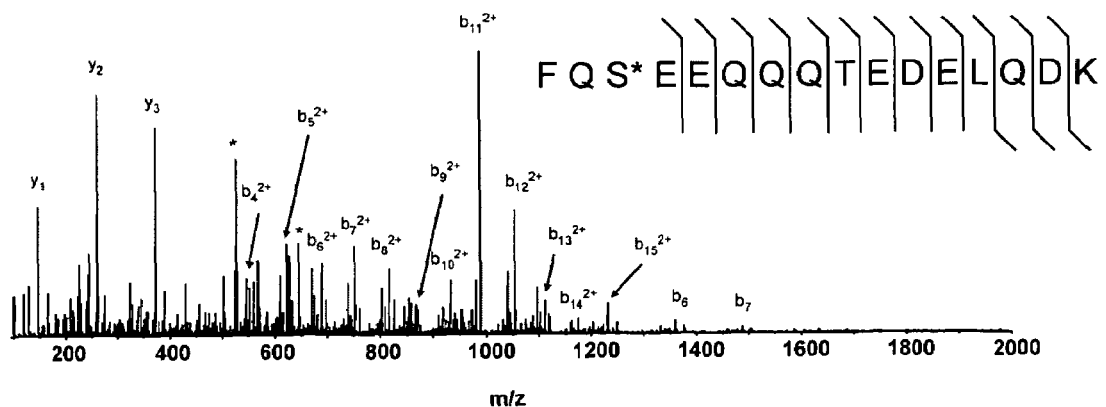
FIG. 3 shows a tandem mass spectrum of the FAT-labeled beta-casein tryptic peptide (SEQ ID NO: 1) acquired by a hybrid-TOF instrument (QSTAR) equipped with a Protana nano-ESI source. Tandem mass spectrum of the same peptide (triply charged) acquired by a hybrid-TOF instrument equipped with the Protana nano-ESI source. The. MS/MS spectrum was searched against the nr database (NCBI) using MASCOT. A custom differential modification of serine or threonine corresponding to FAT-label addition was employed in the search (right).

The derivatized peptide was subsequently analyzed by tandem mass spectroscopy. FIG. 2 illustrates a mass spectrum of the FAT-labeled peptide as acquired by a hybrid-TOF instrument (QSTAR) equipped with an oMALDI source. Examples of FAT fragment ions that could be used as diagnostic ions for precursor ion scanning are indicated. FIG. 3 depicts a mass spectrum of the same FAT-labeled peptide as acquired by a hybrid-TOF instrument (QSTAR) equipped with a Protana nano-ESI source. The MS/MS spectrum was searched against the nr database (NCBI) using MASCOT. A custom differential modification of serine or threonine corresponding to FAT-label addition was employed in the search. The search correctly identified the FAT-labeled peptide (FQSEEQQQTEDELQDK-SEQ ID NO: 1) and the source (beta-casein).

EXAMPLE 3

In-Gel Fluorescence Detection and Proteolytic Digestion Followed by Affinity Purification and Analysis by Mass Spectroscopy A sample of beta-casein protein was subjected to conditions appropriate for beta-elimination of phosphate. After incubation for 1-2 hours at room temperature, Michael addition of the FAT reagent was carried out for an additional 3-6 hours at room temperature.

Figure 4:
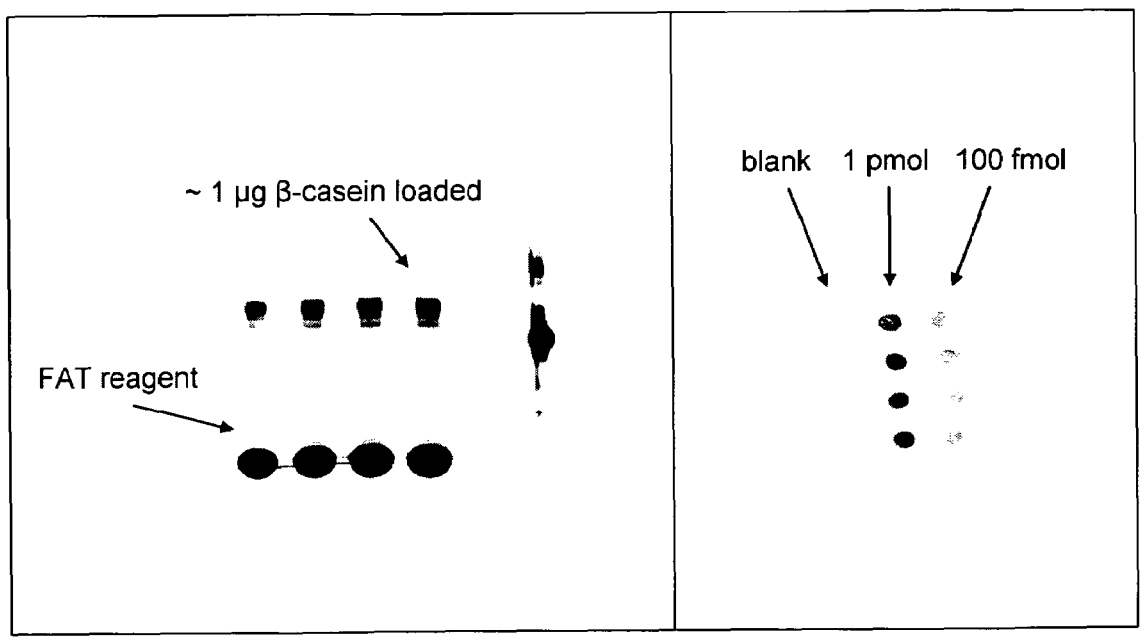
FIG. 4 presents fluorescence images generated from the Typhoon 8600 instrument. Images portrayed are (1) intact FAT-labeled phosphoprotein after 1D SDS-PAGE separation (left) and (2) a MALDI plate spotted with varying concentrations of the FAT reagent (right).

Following labeling of the beta casein protein, the protein mixture was separated by 1D SDS-PAGE and the gel was analyzed by a Typhoon 8600 variable mode imager (Amersham Pharmacia Biotech) to map the presence of FAT-labeled phosphoproteins present in the sample. FIG. 4 shows an example of an SDS-PAGE gel containing FAT-labeled beta-casein as imaged by the Typhoon 8600 instrument. Also illustrated is a MALDI plate spotted with different quantities of the FAT reagent alone and imaged by the Typhoon 8600 instrument to demonstrate the sensitivity of the technique to small quantities of FAT label.

Bands that produced a fluorescent signal were digested in-gel with Lys-C (Roche Applied Science). Following the digestion procedure, the digested bands were (1) purified with either a C18 ZipTip or an anti-rhodamine microaffinity column and (2) analyzed by a quadrupole time-of-flight instrument (QSTAR, Applied Biosystems) operated with either MALDI or nano-ESI ionization sources. General screening of reaction progress was performed by a MALDI-TOF instrument (Voyager DE-Pro, Applied Biosystems).

Figure 5:
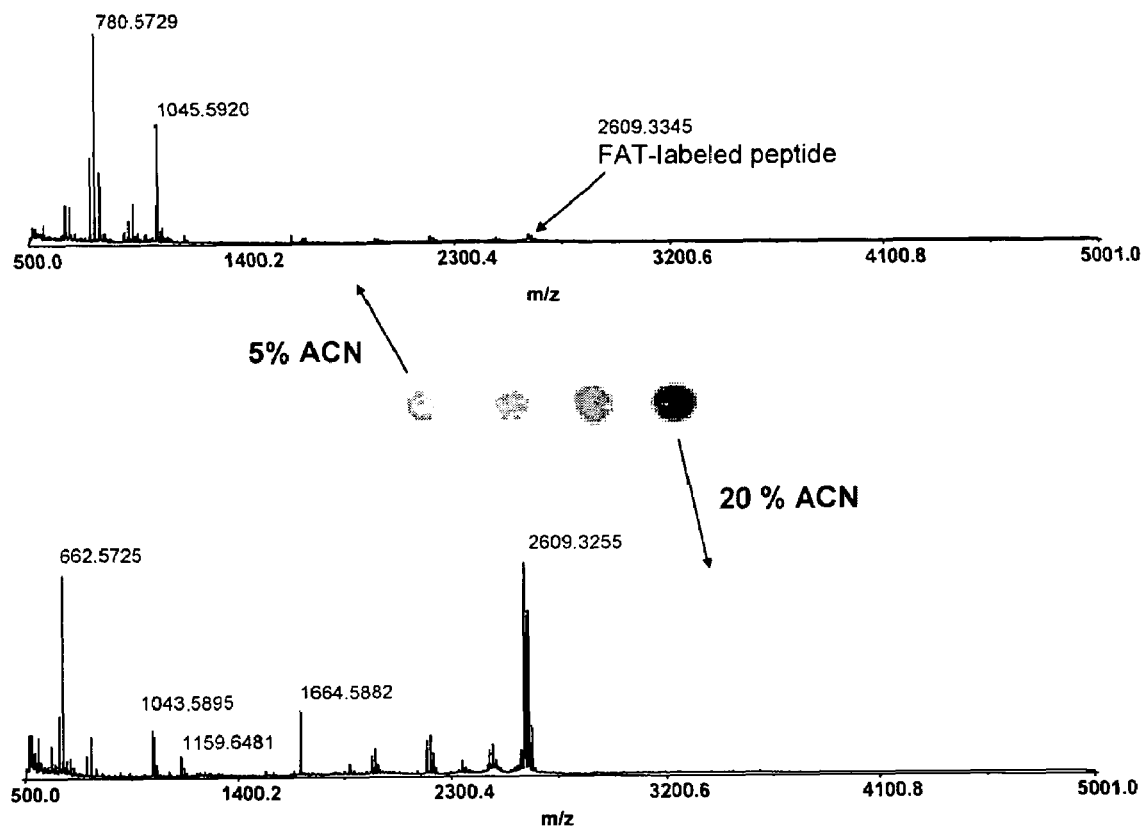
FIG. 5 provides mass spectra of FAT-labeled beta casein that was digested in-gel with Lys-C, loaded onto a C18 Zip-Tip, and fractionated with varying concentrations of acetonitrile onto a MALDI plate. In conjunction with fluorescence imaging, this technique allows for selective targeting of FAT-labeled peptides after fractionation of complex mixtures.

For digested bands purified by ZipTip, FIG. 5 shows mass spectra obtained for ZipTip elution fractions obtained at varying concentrations of acetonitrile. A Typhoon 8600 image overlaid on the figure shows that the fraction eluted with 20% acetonitrile is more highly fluorescent than the fraction eluted with 5% acetonitrile. The corresponding mass spectra show that the more highly fluorescent fraction contains a greater concentration of derivatized (FAT labeled) peptide. Together these data provide an example of the utility of the FAT label for selective fluorescence-based targeting of FAT-labeled (formerly phosphorylated) peptides after fractionation of complex mixtures.

Figure 7:
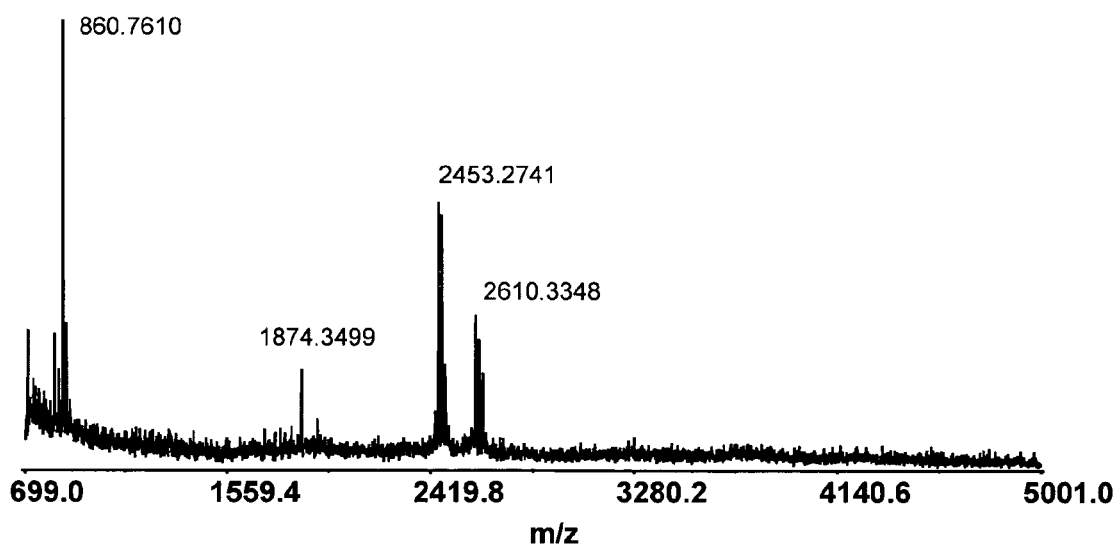
FIG. 7 illustrates a mass spectrum showing the enrichment of FAT-labeled peptides after affinity purification of the beta casein Lys-C digest.

For digested bands purified by affinity chromatography, an anti-rhodamine microaffinity column was prepared as noted previously. The peptide mixture from the digested gel band was dispensed through the microaffinity column several times to ensure maximum binding. The column was washed several times with 10 µL PBS to remove nonspecifically bound peptides. After 3×10 µL washes of water to remove excess salt, FAT-labeled peptides were eluted from the column with 2 µL of 2% TFA directly onto a MALDI plate. FIG. 7 shows the MALDI-TOF mass spectrum in which the affinity enrichment of FAT-labeled peptide is apparent. This provides an example of the utility of the FAT label for selective affinity-based purification of FAT-labeled (formerly phosphorylated) peptides.

EXAMPLE 4

Synthesis of N$^\alpha$[tetramethylrhodamine 5(6)-carboxamide]-Arginyl-cysteamine N$^\alpha$Fmoc-Arg(Pbf)-OH was coupled to cysteamine-2-chlorotrityl resin (Novobiochem) with dicyclohexycarbodiamide in the presence of 1-hydroxybenzotriazole. The protecting group was removed by 20% piperidine in dimethylforamide (DMF) and then subsequently coupled with 5(6)-carboxytetramethylrhodamine N-hydroxysuccinimide ester in the presence of 1-hydroxybenzotriazole in DMF. The peptide resin was washed with DMF, dichloromethane, methyl alcohol, dichloromethane, ether, and then dried. The peptide was then cleaved from the resin with trifluoroacetic acid (TFA) containing 5% triisopropylsilane and 5% water at room temperature for 1 hour. The resin/TFA mixture was filtered into cooled tert-butyl methyl ether. The precipitated peptide was separated by centrifugation and washed three times with fresh tert-butyl methyl ether. The peptide derivatives were then purified by reversed phase (C18) HPLC.

---

---

We claim:

1. An isolated compound of the formula:

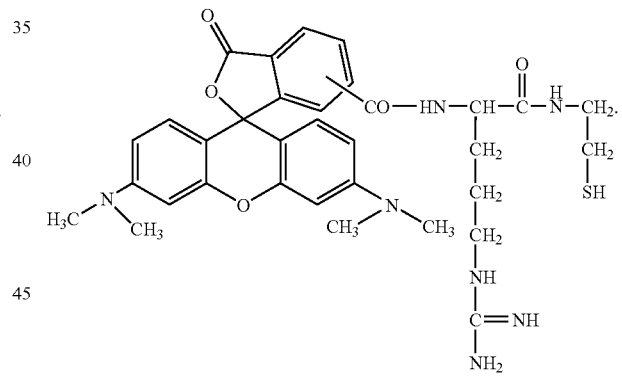

2. An isolated compound comprising a cysteamine moiety covalently attached to a discriminating moiety selected from:
   a) fluorophores;
   b) chromophores;
   c) magnetic particles;
   d) gold particles; or
   e) isotopic mass labels.

3. The isolated compound according to claim 2, wherein said discriminating moiety is a fluorophore.

4. The isolated compound according to claim 3, wherein said fluorophore is rhodamine, fluorescein, coumarin, eosin, erythrosin, lucifer yellow, malachite green, or oregon green.

5. A composition comprising a carrier and a compound comprising a cysteamine moiety covalently attached to a discriminating moiety selected from:
   a) fluorophores;
   b) chromophores;

c) magnetic particles;
d) gold particles; or
e) isotopic mass labels.

6. The composition according to claim 5, wherein said compound is

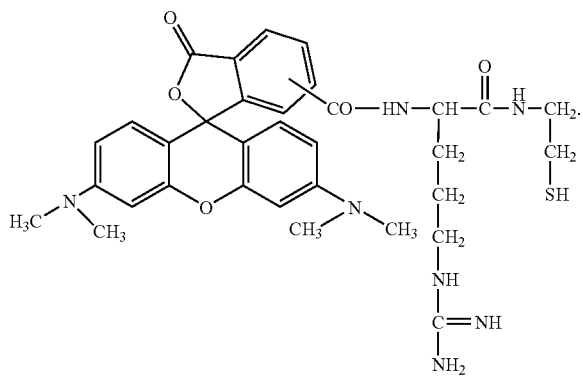

7. The isolated compound according to claim 2, wherein said discriminating moiety is not covalently attached to the cysteamine moiety through the sulfur atom.

8. The isolated compound according to claim 2, wherein said discriminating moiety is a fluorophore.

9. The isolated compound according to claim 2, wherein said discriminating moiety is a chromophore.

10. The isolated compound according to claim 2, wherein said discriminating moiety is a magnetic particle.

11. The isolated compound according to claim 2, wherein said discriminating moiety is a gold particle.

12. The isolated compound according to claim 2, wherein said discriminating moiety is an isotopic mass label.

13. The isolated compound according to claim 7, wherein said discriminating moiety is a fluorophore.

14. The isolated compound according to claim 7, wherein said discriminating moiety is a chromophore.

15. The isolated compound according to claim 7, wherein said discriminating moiety is a magnetic particle.

16. The isolated compound according to claim 7, wherein said discriminating moiety is a gold particle.

17. The composition according to claim 5, wherein said compound comprises a cysteamine moiety covalently attached to a fluorophore.

18. The composition according to claim 5, wherein said compound comprises a cysteamine moiety covalently attached to a chromophore.

19. The composition according to claim 5, wherein said compound comprises a cysteamine moiety covalently attached to a magnetic particle.

20. The composition according to claim 5, wherein said compound comprises a cysteamine moiety covalently attached to a gold particle.

21. The composition according to claim 5, wherein said discriminating moiety is a covalently attached isotopic mass label.

22. The composition according to claim 17, wherein said fluorophore is not covalently attached to the cysteamine moiety through the sulfur atom.

23. The composition according to claim 18, wherein said chromophore is not covalently attached to the cysteamine moiety through the sulfur atom.

24. The composition according to claim 19, wherein said magnetic particle is not covalently attached to the cysteamine moiety through the sulfur atom.

25. The composition according to claim 20, wherein said gold particle is not covalently attached to the cysteamine moiety through the sulfur atom.

26. The isolated compound according to claim 2, wherein said compound is

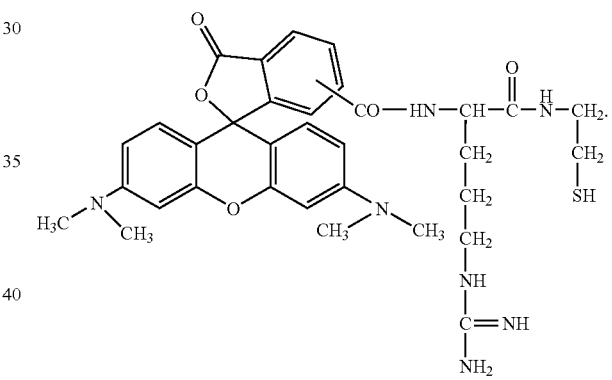

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: FAT-Labeled HPLC-Purified Tryptic
      Phosphopeptide of beta-Casein
<220> FEATURE:
<221> NAME/KEY: MISC_FEATURE
<222> LOCATION: (1)..(16)
<223> OTHER INFORMATION: See Example 2 and Figures 2-3.

<400> SEQUENCE: 1

Phe Gln Ser Glu Glu Gln Gln Gln Thr Glu Asp Glu Leu Gln Asp Lys
1               5                   10                  15
```